United States Patent [19]

Bleha et al.

[11] 4,085,005
[45] Apr. 18, 1978

[54] METHOD OF PREPARATION OF INSOLUBLE BIOLOGICALLY ACTIVE COMPOUNDS

[75] Inventors: Miroslav Bleha; Eva Votavová; Zdeněk Plichta, all of Prague, Czechoslovakia

[73] Assignee: Ceskoslovenska akademie ved, Prague, Czechoslovakia

[21] Appl. No.: 669,866

[22] Filed: Mar. 24, 1976

[30] Foreign Application Priority Data

Mar. 27, 1975 Czechoslovakia ............... 2132/75

[51] Int. Cl.² .............................................. C07G 7/02
[52] U.S. Cl. .................................... 195/68; 195/63; 195/DIG. 11; 424/12; 526/312
[58] Field of Search ............... 195/68, 63, DIG. 11, 195/103.5 R; 526/312; 424/12

[56] References Cited

U.S. PATENT DOCUMENTS

| 3,706,633 | 12/1972 | Katchalski et al. ............... 195/63 |
| 3,745,088 | 7/1973 | Mehltretter et al. ............ 195/63 |
| 3,970,521 | 7/1976 | Zaborsky et al. ................ 195/63 |

OTHER PUBLICATIONS

Zaborsky, "Immobilized Enzymes", published by CRC Press, (1974), pp. 17, 18 and 37.

*Primary Examiner*—Alvin E. Tanenholtz
*Assistant Examiner*—C. A. Fan

[57] ABSTRACT

The invention relates to biologically active insoluble compounds on a carrier containing in its side chains a p-phenylene-diamine skeleton, where a polymer of the general formula I

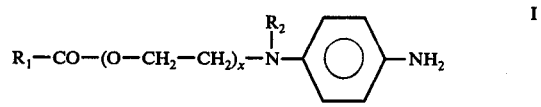

where $R_1$ is a polymer residue, $R_2$ is a lower alkyl group, $x = 1$–$4$, is oxidized in the presence of a soluble biologically active compound containing a primary amino group, such as e.g. enzymes, coenzymes, inhibitors of enzymes, hormones, or antigens. The oxidation is carried out by using an oxidation agent which does not disturb the biologically active compounds present in the mixture.

8 Claims, No Drawings

METHOD OF PREPARATION OF INSOLUBLE BIOLOGICALLY ACTIVE COMPOUNDS

The invention relates to the preparation of insoluble biologically active compounds, such as enzymes, coenzymes, inhibitors of enzymes, hormones, antigens etc. by bonding soluble biologically active compounds containing one or more than one primary amino groups to a defined reactive polymeric carrier prepared by copolymerization of suitable monomers as described in copending application Ser. No. 625,317, filed Oct. 23, 1975 and assigned to the same assignee.

The insoluble biologically active compounds are increasingly widely applied in a number of application procedures. Various methods of using them have been developed; they are particularly widely applied in affinity chromatography, both analytical and preparative.

In recent years a number of methods of preparation of such compounds have been developed. This is primarily connected with the preparation of suitable carriers, predominantly of the polymer type, and with a modification thereof leading to the possible bonding of the active compound. There are two routes for achieving this aim: Either by preparing the copolymer from suitable monomers, so that a matrix is obtained to which a biologically active compound can be bonded by a simple procedure, or the polymer contains suitable reaction sites which by chemical modification can assume a form allowing bonding of the active compound.

There are several methods leading to the formation of the covalent bond carrier-biological sample. The decisive role for a good functioning of the fixed sample is played by an unperturbed site which determines the activity of the compound. All conditions of bond formation must therefore be subjected to this fact.

The biologically active compounds are in most cases chemically fixed by means of one of the free primary amino groups. A reactive site on the carrier capable of reacting with the amino group is formed e.g. by a reaction of the hydroxylic group with bromine cyanide, phosgene, thiophosgene, while giving rise to an unstable intermediate. By diazotizing the aromatic primary amino group in the polymer it is possible to prepare a diazonium salt, which by coupling with an active compound containing a suitable aromatic system also yields the covalent bond. The above methods of preparation of biologically active insoluble compounds require the use of dangerous compounds for reactions leading to the formation of the reactive site on the polymer. This group comprises reactions of bromine cyanide, phosgene, thiophosgene, etc. Moreover, the carriers thus modified are rather unstable both thermally and chemically and require fast operations, in particular careful washing in order to remove the residues of reagents which may be dangerous for the biological activity of further reacting compounds.

The objective of the invention is the preparation of insoluble biologically active compounds by bonding soluble biologically active compounds to a defined polymer carrier containing in its side chains the p-phenylenediamine skeleton as the active bonding site. The system can be represented by the following formula:

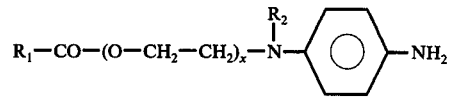

where $R_1$ is a polymer residue, $R_2$ is a lower alkyl group, $x = 1-4$. Oxidation of the above aromatic system yields a reactive form capable of reacting with the amino group of the biologically active compound with formation of a strong covalent bond. The oxidations are carried out in an aqueous medium in the presence of the biologically active compound and under suitable conditions of pH values. Various oxidizing agents can be used which do not interfere with the biologically active compounds present in the reaction mixture, such as e.g. potassium ferricyanide, $Cu^{2+}$ ions in an alkaline medium, or in other words, complex forms of the redox ions, and also e.g. the arsenate of an alkali metal, or a compound possessing a similar redox potential.

It is also possible to work under biologically tolerable conditions in a suitable medium, with oxygen (also air oxygen) being the oxidation agent in the presence of ions suitable for redox systems, such as e.g. $Cu^{2+}$ ions in an alkaline medium or a cupric ammonium complex. Organic redox systems, such as quinone — hydroquinone, can also be used in the reactions.

The temperature of the oxidation reactions is predominantly defined by the thermal stability of the biologically active compounds and varies within a range of $-5°$ to $+10°$ C, advantageously from $0°$ to $5°$ C.

The above type of biologically active compounds can be advantageously prepared using hydrophilic copolymers in various forms, such as copolymers soluble in water or crosslinked in the form of blocks, plates, tubes, etc. For uses of the biologically active compounds in various applications, crosslinked copolymers having a porous character in the form of spherical particles have proved to be of advantage. Such materials possess a high specific surface area and thus, after bonding of the biologically active compounds, also a rather high effectivity. They are therefore used in various application processes, such as various forms of affinity chromatography, separation and purification processes, and the like.

The invention is further illustrated by the following examples without limiting the objective of the invention by these examples.

EXAMPLE 1

The polymer carrier was prepared by heterogeneous suspension copolymerization from a mixture of monomers consisting of glycol monomethacrylate, glycol dimethacrylate and N-ethyl-N-(2-methacroylethyl)-N'-acetyl-p-phenylenediamine so that the final product contained 14% of the functional monomer and had a porous character with a specific surface area of 65.6 m²/g. After acid hydrolysis, 0.5 g of the material was suspended in 10 ml of a 0.05 mol borax solution containing 40 mg of trypsin. 2 ml of a 0.01 mol solution of potassium ferricyanide in a 0.05 mol borax solution were added to the suspension during 1 hour. The gel material with bonded enzyme was then washed by standard procedure with 1 N NaCl containing 0.1 N acetate buffer solution, pH = 4.7, and eventually with 0.01 N acetate buffer solution. The activity of the bonded enzyme was determined, (6.7 milliunits/mg) and the bond strength was checked by determining bonded amino acids after washing of the enzyme with a solution of 6 N guanidine hydrochloride.

EXAMPLE 2

0.5 g of the polymer carrier used in example 1 was employed for bonding glucose oxidase. 40 mg of glucose oxidase in 10 ml of a 0.05 mol borax solution was mixed with the polymer and oxidized for 1 hour with 2 ml of ferricyanide in 0.05 mol solution in borax. After removal of the reaction medium by filtration the polymer material was washed with a solution of 1 N NaCl in 0.1 N NaHCO$_3$, distilled water, and transferred into 0.1 mol of phosphate buffer solution. The activity of bonded glucose oxidase thus determined was 18.7 milliunits/mg.

EXAMPLE 3

A polymer carrier used in the preparation of bonded chymotrypsin was prepared according to Example 8 of copending application Ser. No. 625,317. After washing with distilled water and ethanol it was treated by acid hydrolysis in dilute hydrochloric acid. After washing the polymer was mixed (0.5 g of polymer) with 50 mg of chymotrypsin dissolved in an ammonium buffer solution pH = 10 in the presence of Cu$^{2+}$ ions. The mixture was stirred under access of air. The initial pH was kept constant by adding sodium carbonate. After two hours of reaction the reaction mixture was filtered, and the activity of the bonded chymotrypsin was determined on washing (6.24 units A$_{280}$/min mg 10$^4$).

EXAMPLE 4

The polymer carrier prepared as in Example 1 was used for bonding trypsin. 0.5 g of the polymer was mixed with a solution of 50 mg trypsin in 5 ml of distilled water. 5 ml of ammonium buffer solution containing 22 mg of hydroquinone was added, and stirring was continued at 5° C for 3 hours under access of air. The polymer material was washed, and the activity of the bonded trypsin was determined (5.06 milliunits/mg).

EXAMPLE 5

Pepsin was bonded onto the polymer prepared in Example 3 in 1 mol of acetic acid, by way of oxidation reaction with quinone as the oxidation agent.

EXAMPLE 6

Chymotrypsinogen was bonded onto the polymer prepared in Example 3 in 0.1 N NaHCO$_3$ by oxidation with ferricyanide according to example 1. The properties of the product were investigated by spectrofluorimetry in the UV region. The amount of the bonded chymotrypsinogen was 100 mg/g of polymer.

EXAMPLE 7

Trypsin was bonded onto the polymer carrier prepared in Example 1 by oxidation reaction with potassium arsenate in a 0.05 mol borax solution. On washing by the prescribed procedure the enzymatic activity of bonded trypsin was determined (6.2 milliunits/mg).

EXAMPLE 8

Chymotrypsinogen was bonded onto the polymer prepared in Example 3 by oxidation reaction with the access of air in the presence of a cupric ammonium complex at pH = 11. The mixture was stirred at 0°-5° C for 3 hours. On washing of the polymeric material the amount of the bonded compound was determined. The amount of bonded chymotrypsinogen was 120 mg/g of polymer.

EXAMPLE 9

A polymerization mixture consisting of 2 g cyclohexanol, 1 g lauryl alcohol, 2 g ethyleneglycol monomethacrylate, 0.5 g N-ethyl-N-(2-methacroylethyl)-N'-acetyl-p-phenylenediamine, 0.5 g ethyleneglycoldimethacrylate and 0.015 g AIBN (azobisisobutyronitrile) was polymerized at 55° C for 6 hours between planeparallel plates to a porous layer, 1 mm thick. The specific surface area of the material thus prepared is 0.8 m$^2$/g. Onto the material thus prepared, after acid hydrolysis glucose oxidase in a 0.05 mol borax solution was bonded by oxidation with ferricyanide according to Example 2. The activity of the bonded glucose oxidase was 4.7 milliunits/mg.

We claim:

1. A method of insolubilizing a soluble biologically active compound, which comprises providing an alkaline aqueous medium containing (1) a polymeric material having p-phenylenediamine reactive sites according to the general formula:

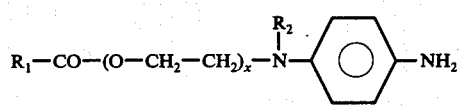

wherein R$_1$ is a polymer residue, R$_2$ is a lower alkyl group, and $x$ is 1 to 4, and (2) a soluble biologically active compound having a primary amino group; and oxidatively coupling the amino group of said soluble biologically active compound to the polymeric material by means of oxidizing said reactive sites with an agent that does not affect the biological activity of the biologically active compound and which is selected from the group consisting of alkali metal arsenates, ferricyanides, quinone, oxygen together with cupric ions, a cupric ammonium complex and hydroquinone.

2. A procedure according to claim 1, in which the oxidative coupling is carried out at a temperature of −5° C. to +10° C.

3. A procedure according to claim 2, in which the temperature is 0° to 5° C.

4. A procedure according to claim 1, in which the biologically active compound is an enzyme.

5. A procedure according to claim 1, in which the biologically active compound is a coenzyme.

6. A procedure according to claim 1, in which the biologically active compound is an enzyme inhibitor.

7. A procedure according to claim 1, in which the biologically active compound is a hormone.

8. A procedure according to claim 1, in which the biologically active compound is an antigen.

* * * * *